United States Patent [19]

Zhang et al.

[11] Patent Number: 5,128,476

[45] Date of Patent: Jul. 7, 1992

[54] BIOTINYLATED OLIGONUCLEOTIDES AND REAGENTS FOR PREPARING THE SAME

[75] Inventors: Guangrong Zhang; Richard V. Case, both of Midland, Tex.

[73] Assignee: The Midland Certified Reagent Company, Midland, Tex.

[21] Appl. No.: 658,242

[22] Filed: Feb. 20, 1991

[51] Int. Cl.$^5$ ............................. C07F 9/06; C07F 9/28
[52] U.S. Cl. ...................................... 548/113; 536/27
[58] Field of Search .......................................... 548/113

[56] References Cited

U.S. PATENT DOCUMENTS

| | | | |
|---|---|---|---|
| 4,707,440 | 11/1987 | Stavrianopoulos | 548/114 |
| 4,711,955 | 12/1987 | Ward et al. | 548/114 |
| 4,908,453 | 3/1990 | Cocuzza | 548/113 |
| 5,002,885 | 3/1991 | Stavrianopoulos | 548/114 |
| 5,013,831 | 5/1991 | Stavrianopoulos | 548/114 |

*Primary Examiner*—Johann Richter
*Attorney, Agent, or Firm*—Oblon, Spivak, McClelland, Maier & Neustadt

[57] ABSTRACT

Reagents of the formula I

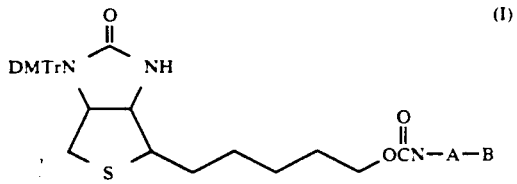

wherein A is $-(CH_2)_m-O-$ (m=2 to 20) or $-(C_nH_{2n}-O)_t-$ (n=2 to 6; t=2 to 10) and B is selected from the group consisting of

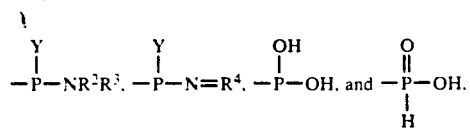

and salts thereof are useful for the preparation of 5'-biotinylated oligonucleotides.

4 Claims, No Drawings

BIOTINYLATED OLIGONUCLEOTIDES AND REAGENTS FOR PREPARING THE SAME

BACKGROUND OF THE INVENTION

1. Field of the Invention

The present invention relates to biotinylated oligonucleotides and reagents for preparing biotinylated oligonucleotides.

2. Discussion of the Background

The use of labeled oligonucleotides as hybridization probes is widespread. Although labeling of the probes with the isotope $^{32}P$ is common, such probes may also be labeled with biotin, which may be detected as a result of its binding to avidin and streptavidin. The use of a biotin-labeled (biotinylated) probe avoids the problems encountered with radioactive labels such as $^{32}P$.

Recently there have been reports of oligonucleotides to which biotin has been covalently attached to the 5'-hydroxyl group (see: Chollet et al, Nucleic Acids Res., vol. 13, p. 1529 (1985); Wachter et al. Nucleic Acids Res., vol. 14, p. 7985 (1986); Agarawal et al. Nucleic Acids Res., vol. 14, p. 6227 (1986); Urdea et al, Nucleic Acids Res., vol. 16, p. 4937 (1988); and Cook et al. Nucleic Acids Res., vol. 16, p. 4077 (1988). However, all of these methods required special reagents and considerable time and effort.

Biotinylated oligonucleotides have also been demonstrated to have utility in ligase-medicated gene detection (Landergreu et al, Science. vol. 241, p. 1077 (1988)), sequencing after amplification by the polymerase chain reaction (PCR) (Mitchell et al, Anal. Biochem., vol. 178, p. 239 (1989)), and nonradioactive sequencing of DNA (Richterich, Nucleic Acids Res., vol. 17, p. 2181 (1989)).

Cocuzza has reported reagents, which can be used in conjunction with automated solid state synthetic technique, for the preparation of 5'-biotinylated oligonucleotides (Cocuzza. Tetrahedron Letters. vol. 30, pp. 6287–6290 (1989) and U.S. Pat. No. 4,908,453). However, the biotinylated oligonucleotides afforded by this approach are not stable to the standard workup procedures required to remove the protecting groups commonly used in solid state oligonucleotide synthesis.

Alves et al have also described a chemical method of labelling oligonucleotides with biotin (Alves et al, Tetrahedron Letters, vol. 30, pp. 3089–3092 (1989)). However, the exemplified reagents possess a short linkage between the phosphoramiditic group and the biotinyl residue.

Furthermore, both the reagents above utilize solvents not ordinarily employed for DNA synthesis, namely dimethylformamide (Cocuzza) and a mixture of dichloroethane and acetonitrile (Alves et al), a further disadvantage in both reagents.

Miyoshi et al (U.S. Pat. No. 4,605,735) disclose a process for preparing oligonucleotide derivatives in which biotin is bonded to the terminal amino group of an oligonucleotide derivative. However, the method of coupling biotin to the DNA requires a separate manual synthesis reaction, after prior preparation of the DNA oligonucleotide.

Carr et al (European Patent Application 202,758) disclose a solid-state method for preparing 5'-biotinylated oligonucleotides by reacting the deprotected 5'-hydroxy group with a phosphorylated biotin derivative. Kempe et al (Nucleic Acids Res., vol. 13, p. 45 (1985)) also disclose a solid state synthesis of 5'-biotinylated oligonucleotides, in which the deprotected 5'-hydroxy group is reacted with p-chlorophenylphosphoditriazolide, the product is hydrolyzed, and the hydrolyzed product is reacted with 2-(biotinylamido)ethanol. Both of these methods suffer from the disadvantages of requiring special reagents. Further, in the case of Kempe et al, the product contains the labile amide linkage.

Levenson et al (U.S. Pat. No. 4,751,313) disclose a method for labelling an oligonucleotide with biotin using a biotin derivative which contains an alkylating intercalation moiety. However, the product of this process is not a 5'-biotinylated oligonucleotide Ward et al (U.S. Pat. No. 4,711,955) disclose the preparation of labeled nucleotides in which biotin is bonded to the nucleotide via a base (purine, 7-deazapurine, or pyrimidine moiety). Again, the products are not 5'-biotinylated oligonucleotides.

Accordingly, there remains a need for 5'-biotinylated oligonucleotides and reagents for their preparation which do not suffer from the above-mentioned drawbacks.

SUMMARY OF THE INVENTION

Accordingly, it is an object of the present invention to provide novel biotinylated oligonucleotides in which the linkage between the biotin moiety and the oligonucleotide is stable to conditions normally encountered during the solid state synthesis of oligonucleotides.

It is another object of the present invention to provide novel biotinylated oligonucleotides which are stable to the deprotection conditions commonly used in solid state oligonucleotide synthesis.

It is another object of the present invention to provide novel biotinylated oligonucleotides which bind efficiently with compounds such as avidin.

It is another object of the present invention to provide novel reagents for the preparation of such biotinylated oligonucleotides.

It is another object of the present invention to provide reagents, for the biotinylation of oligonucleotides, which can be conveniently used in solid state synthesis.

It is another object of the present invention to provide a method for preparing such oligonucleotides.

These and other objects, which will become apparent during the following detailed description, have been achieved by the inventors discovery that reagents of the formula (I):

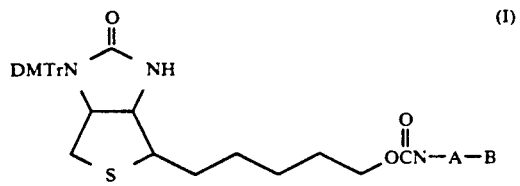

in which DMTr represents the 4,4'-dimethoxytrityl group, A is a $-(CH_2)_m-)-$ group (wherein m is an integer of from 2 to 20) or a $-(C_nH_{2n}O)_t-$ group (wherein m is an integer of from 2 to 6 and t is an integer of from 2 to 10) and B is a group selected from the group consisting of

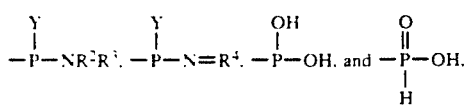

and salts thereof (wherein $R^2$ and $R^3$ are independently selected from the group consisting of $C_{3-10}$ branched alkyl groups and $C_{1-12}$ unbranched alkyl groups; $R^4$ is selected from the group consisting of $-(CRR')_v(X)_r(CRR')_{v'}-$

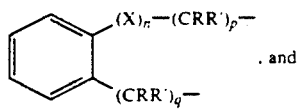

(wherein R and R' are independently selected from the group consisting of H, $C_{3-10}$ branched alkyl groups, $C_{1-10}$ unbranched alkyl groups, $C_{6-10}$ aryl groups, $C_{7-12}$ alkaryl groups and $C_{7-12}$ aralkyl groups; and X is selected from the group consisting of —O—, —S—,

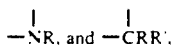

where R and R' are as defined above; v is an integer of 1 to 6, r is an integer of 0 to 1, p is an integer of 1 to 10, and q is an integer of 0 to 10, provided that $2v+r \leq 12$ and $2 \leq r+p+q \leq 13$; and Y is a phosphate protecting group)), may be utilized in solid state oligonucleotide synthesis to afford biotinylated nucleotides of the formula (II):

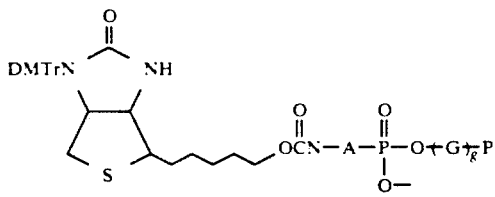

(II)

in which A is defined as above, G is a nucleotide or deoxynucleotide carrying a base selected from the group consisting of adenine, cytosine, guanine, thymine, and hypoxanthine, g is an integer of 1 to 200 and P is H or a polymer.

DETAILED DESCRIPTION OF THE PREFERRED EMBODIMENTS

Thus, one aspect of the present invention relates to compounds of the formula (I):

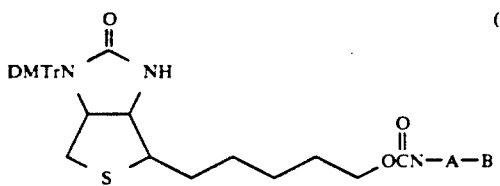

(I)

in which DMTr represents the 4,4'-dimethoxytrityl group, A is a $-(CH_2)_m-O-$ group (wherein m is an integer of from 2 to 20) or a $-(C_nH_{2n})-O-_t$ group (wherein n is an integer of from 2 to 6 and t is an integer of from 2 to 10) and B is a group selected from the group consisting of

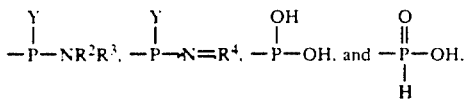

and salts thereof (wherein $R^2$ and $R^3$ are independently selected from the group consisting of $C_{3-10}$ branched alkyl groups and $C_{1-12}$ unbranched alkyl groups; $R^4$ is selected from the group consisting of $-CRR')_v(X)_r(CRR'-_{v'}$

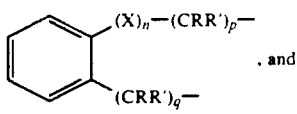

, and

(wherein R and R' are independently selected from the group consisting of H, $C_{3-10}$ branched alkyl groups, $C_{1-10}$ unbranched alkyl groups, $C_{6-10}$ aryl groups, $C_{7-12}$ alkaryl groups and $C_{7-12}$ aralkyl groups; and X is selected from the group consisting of —O—, —S—,

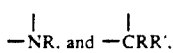

where R and R' are as defined above; v is an integer of 1 to 6, r is an integer of 0 to 1, p is an integer of 1 to 10, and q is an integer of 0 to 10, provided that $2v+r \leq 12$ and $2 \leq r+p+q \leq 12$; and Y is a phosphate protecting group)).

When A is $-(CH_2)_m O-$, it is preferred that m be an integer of 4 to 12, most preferably m is 6. When A is $C_nH_{2n}-O_t$ it is preferred that n is 2 or 3, most preferably n is 2. It is to be understood that when n is greater than 2, the $-C_nH_{2n}-O-_t$ group may be branched group (e.g., isopropylene) as well as unbranched (e.g., propylene). It is preferred that the total number of atoms in the backbone of the $-(C_nH_2-O-)_t$ chain be from 3 to 20, more preferably 3 to 12, most preferably 6. It is preferred that A is a $-(CH_2)_m O-$ group.

It is to be understood that when B is $-P(OH)_2$ (phosphorous acid) it is in equilibrium with $-HP(=O)(OH)$ (H-phosphonate). It is preferred that B is

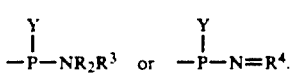

These reagents are known as phosphoramidite reagents and can be synthesized by a number of conventional methods (see, e.g., Barone et al, *Nucleic Acids Res.*, vol. 12, p. 4051 (1984) incorporated herein by reference). The H-phosphonates can be prepared from alcohols by conventional methods (see, e.g., Froehler et al. *Nucleic Acids Res.*, vol. 4, p. 5399 (1986) and Sinha et al, *Nucleic Acids Res.*, vol. 16, p. 2659 (1988), which are incorporated herein by reference).

As noted above, it is preferred that B is

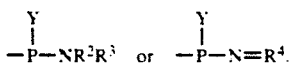

In these groups, Y is any phosphate protecting group. Preferred Y groups include 4—Cl—C$_6$H$_4$—o—; 2—

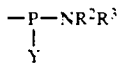

and R$^2$ and R$^3$ are —CH(CH$_3$)$_2$, and Y is NCCH$_2$CH$_2$O. Thus, the most preferred specific compound is that of formula (III):

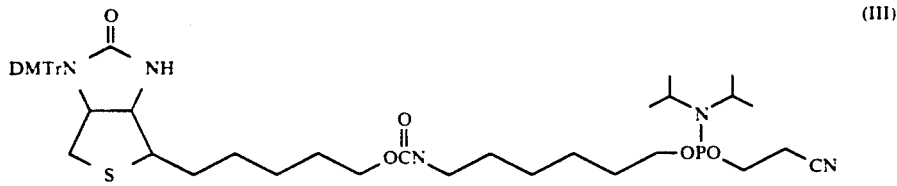

Cl—C$_6$H$_4$—O—; 4NO$_2$—C$_6$H$_4$—O—; 4—NO$_2$—C$_6$H$_4$CH$_2$CH$_2$—o—; 2,4—NO$_2$—C$_6$H$_3$CH$_2$CH$_2$—O—; 2,4—Cl$_2$—C$_6$H$_3$—O—; 2,3—Cl$_2$—C$_6$H$_3$—O—; NCCH$_2$CH$_2$O—; NCCH$_2$C(CH$_3$)$_2$—O—; CH$_3$O—; (Z)$_3$CCH$_2$—O—; (Z)$_3$CC(CH$_3$)$_2$—O—R'S—; R'SCH$_2$CH$_2$—O—; R'SO$_2$CH$_2$—CH$_2$—O—; and R'NH—, wherein Z is selected from the group consisting of Cl, Br, and I, and R' is selected from the group consisting of H, C$_{3-10}$ branched alkyl, C$_{1-10}$ unbranched alkyl, C$_{6-10}$ aryl, C$_{7-12}$ alkaryl, and C$_{7-10}$ aralkyl.

Most preferrably B is

The present compounds may be prepared using conventional reagents and readily available starting materials. The synthesis of the present reagent is illustrated by the exemplary synthesis of the compound of formula (III) given in the scheme shown below:

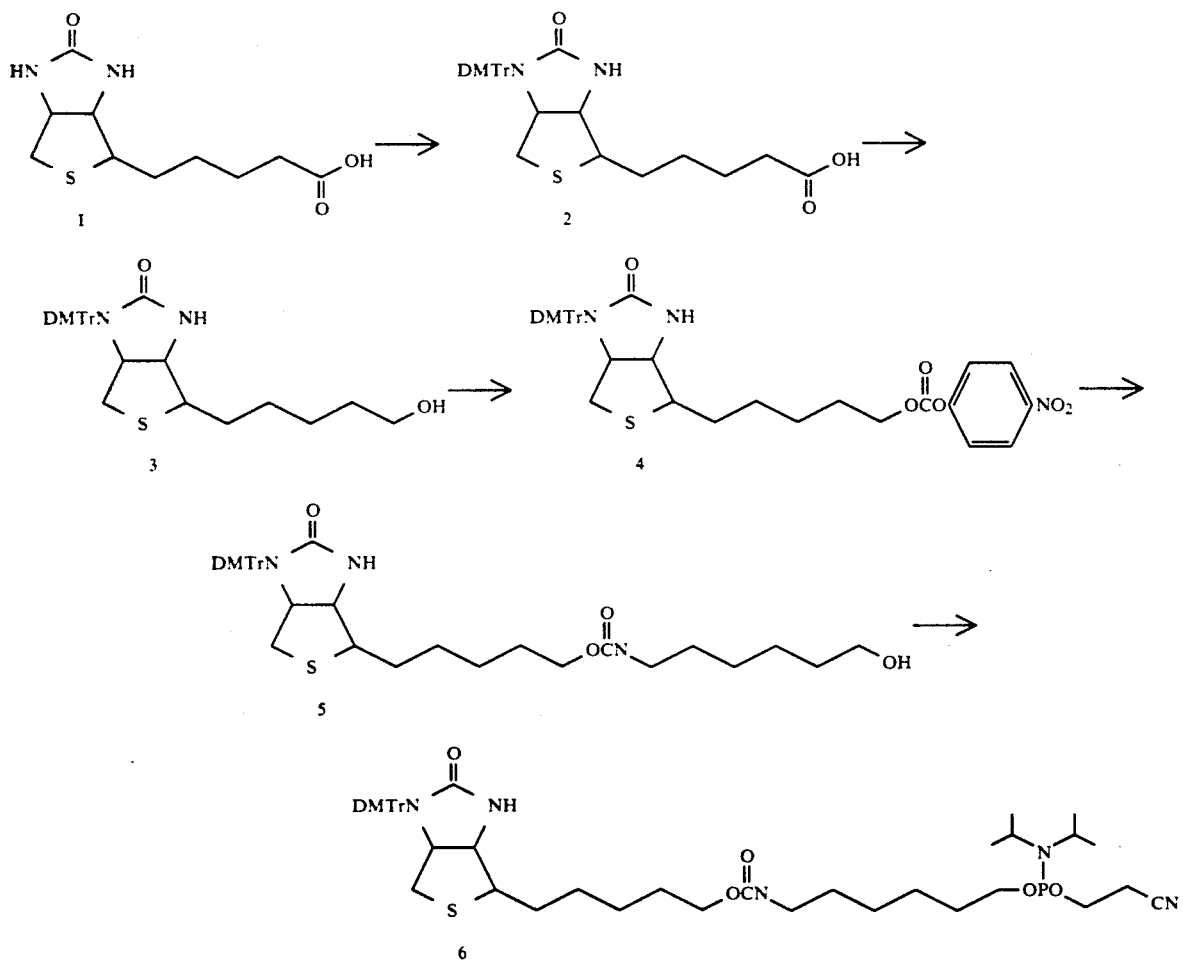

Thus, other examples of the present reagents may be prepared by substituting another compound of the formula NH$_2$—(CH$_2$)$_m$OH (e.g., 3-amino-1-propanol, 4-amino-1-butanol, or 5-amino-1-pentanol) or a compound of the formula H$_2$N—(C$_n$H$_{2n}$—O)$_l$ (e.g., 2-(2-aminoethoxy)ethanol) for the 6-amino-1-hexanol utilized in the conversion of compound 4 to compound 5.

As noted above the derivatives containing the various B groups of the present invention may be prepared by substituting reagents such as chloromethoxymorpholinophosphine, for the 2-cyanoethyl-N,N,N',N'-tetraisopropylphosphorodiamidite used to convert compound 5 to compound 6.

In another aspect, the present invention relates to biotinylated oligonucleotides of the formula (II):

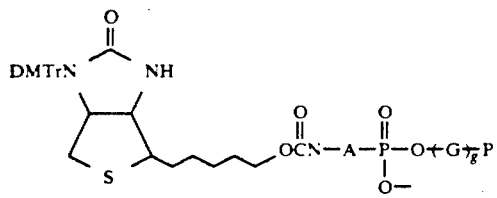

(II)

in which A is defined as above and each G may be the same or different and is at least one nucleotide or deoxynucleotide residue carrying a base selected from the group consisting of adenine, cytosine, guanine, thymine, and hypoxanthine, g is an integer of 1 to 200 preferably 8 to 30, and P is H or a polymer. Suitable polymers include those which may be used in solid-state DNA synthesis, such as silica gel. The present biotinylated oligonucleotides may be prepared by reacting the present biotinylating reagents with an suitably protected nucleotide. A preferred method of preparation is the solid state synthesis as described in U.S. Pat. No. 4,415,732 and PCT application 86-07362, which are incorporated herein by reference. The production of the present oligonucleotides may thus be schematically represented as:

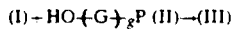

in which P is either H or a polymer support to which the oligonucleotide is attached. It is preferred that the synthesis be carried out in the solid state and that P be a polymer support.

The biotinylated oligonucleotides of the present invention exhibit a number of advantages as compared to conventional biotinylated oligonucleotides. For example, the present biotinylated oligonucleotides are stable under the hydrolysis conditions used to remove the protecting groups commonly used in solid state oligonucleotide synthesis. Thus, one feature of the present invention is the presence of the carbamate group linking the biotinyl residue to -A-. In addition, because the present nucleotide possess the spacer group A, the binding of the labelled oligonucleotide to compounds such as avidin or streptavidin is more efficient.

Other features of the invention will become apparent in the course of the following descriptions of exemplary embodiments which are given for illustration of the invention and are not intended to be limiting thereof.

EXAMPLES

Synthesis of 1-N-(4,4'-Dimethoxytrityl)-D(+)-biotinol (3) from D(+)-biotin(1)

A mixture of D-(+)-biotin 1 (9.76 g, 40 mmole) and pyridine (400 ml) was treated with 4,4'-Dimethoxytrityl chloride (47.46 g, 140 mmole) for 3 days. After removal of the organic solvent under reduced pressure, silica gel (Whatman, DCS-1, $CH_2Cl_2$/MeOH, 9/1, v/v) chromatography of the residue gave 1-N-(4,4'-Dimethoxytrityl)-D(+)-biotin (2). 1-N-(4,4'-Dimethoxytrityl)-D(+)-biotin (2) was reduced in THF by $LiAlH_4$ (3 g, 75 mmole) for 4 h. After removal of the organic solvent under reduced pressure, silica gel (Whatman, DCS-1, $CH_2Cl_2$/MeOH, 9/1, v/v) chromatography of the residue gave 1-N(4,4'-Dimethoxytrityl)-D(+)-biotinol (3), 7.9 g, 37%.

Synthesis of p-Nitrophenyl 1-N-(4,4'-Dimethoxytrityl)-D(+)-biotinolyl Carbonate (4).

A mixture of 1-N-(4,4'-Dimethoxytrityl)-D(+)-biotinol (3) (7.9 g, 14.8 mmole) and p-nitrophenyl chloroformate (4.5 g, 22 mmole) in pyridine (50 ml) and $CH_2Cl_2$ (500 ml) was stirred for 3 hours. After removal of the organic solvent under reduced pressure, silica gel (Whatman, DCS-1, AcOEt) chromatography of the residue gave p-nitrophenyl 1-N-(4,4'-dimethoxytrityl)-D(+)-biotinolyl carbonate (4), 8.4 g, 80%.

Synthesis of 6-[1-N-(4,4'-Dimethoxytrityl)-D(+)-biotinolyl Carbonylamino]-hexanol (5).

p-Nitrophenyl 1-N-(4,4'-dimethoxytrityl)-D(+)-biotinolyl carbonate (4), (8.4 g, 12 mmole) and 6-aminohexanol (2.7 g, 23 mmole) were dissolved in pyridine at room temperature. After 2 hours of reaction, the solvent was removed under reduced pressure, the residue was dissolved in $CH_2Cl_2$ and washed with 5% $NaHCO_3$ and NaCl (sat.). After removal of the organic solvent under reduced pressure, silica gel (Whatman, DCS-1, AcOEt) chromatography of the residue gave 6-[1-N-(4,4'-Dimethoxytrityl)-D(+)-biotinolyl Carbonylamino]-hexanol (4), 4 g, 49.3%.

Synthesis of the Compound of Formula (III) (6)

A solution of (5) (4 g, 5.9 mmole), 2-cyanoethyl-N,N,N',N'-tetraisopropylphosphorodiamidite (2.7 g, 9 mmole) and tetrazole (0.3 g, 4.4 mmole) in $CH_3CN$ was stirred for 4 hours. After the reaction was quenched by the additional of MeOH, the solvent was removed under reduced pressure. The residue was dissolved in $CH_2Cl_2$ and washed with 5% $NaHCO_3$ and NaCl (sat.). After removal of the organic solvent under reduced pressure, silica gel (Whatman, DCS-1, $CH_2Cl_2$/hexane/$Et_3N$, 10/10/1, v/v/v) chromatography of the residue gave the compound of formula (III) (6), 2g, 38.7%.

Biotinylated Oligonucleotide Preparation

The oligonucleotides were synthesized on a 0.2 to 0.4 μmole scale using either a Systec, Inc. Microsyn-1450 synthesizer or an Applied Biosystems, Inc. PCR-Mate 391DNA synthesizer using cyanoethyl phophoramidite chemistry. The dimethoxytrityl group cleaved during each cycle of the synthesis was collected and its absorbance measured to determine the coupling efficiency for the synthesis. Following the syntheses, the oligonucleotides were deprotected with concentrated ammonium hydroxide at 65° C. for 2 hrs. After cooling, this hydrolyzate was subjected to gel filtration on a column (0.8×2.5 cm) of Sephadex G-25. This separates the DNA from ammonia and the protecting groups. The oligonucleotides were then further purified and analyzed using a Perkin-Elmer Series 410 HPLC equipped with a Sorbax Oligo Bio Series anion exchange column (0.2 mm × 8 cm). Separation of oligonucleotides on this column based on the total net negative charge is achieved using a linear gradient between 0.05M sodium phosphate (pH 5.8) containing 6.0M urea and 0.05M sodium phosphate (pH 5.8)+1.0M sodium sulfate containing 6.0M urea. The indicated fractions in the elution profile were then desalted on a Bio-Gel P-4 gel filtration column (1.6×25 cm).

Comparative Example I

Oligonucleotide I (TTTTTCACACACACAC) was manually biotinylated in a post-synthesis reaction. The oligonucleotide had an amino hexyl extender arm (Glen Research) added as the last step of the synthesis. The coupling yield for synthesis was 99.2%. The oligonucleotide was hydrolyzed and gel filtered as described. The fractions containing significant amounts of absorbance at 260 nm were pooled and lyophilized. This material was dissolved in 50 μl of 0.5M triethanolamine. An equal volume of 30 mg/ml biotinamidocaproate N-hydroxysuccinimide ester (Sigma) in dioxane was added and incubated at 4° C. for 15 hrs. The sample was applied to a Sephadex G-25 gel filtration column followed by HPLC as previously described. The anion exchange HPLC elution profile exhibits one major peak.

Examples II and III

Oligonucleotide II (CTAAAGG-GAACAAAAGCTGGA) was biotinylated with the compound of formula III. The coupling yield for the complete synthesis was 96.2% and 96% for the biotinylation step. Oligonculeotide III (CTCTGCTCCGCCACCGGCTT) was biotinylated using a second batch of the compound of formula III. The coupling yield for the complete synthesis was 98.5% but only 87% for the biotinylation step. These oligonucleotides were hydrolyzed, gel filtered and purified by anion exchange HPLC as previously described. The anion exchange HPLC elution profile of Oligonucleotide II shows one major peak, while that of Oligonucleotide III exhibits two major peaks.

All three oligonucleotides including the two peaks of oligonucleotide III were analyzed for the presence of biotin using two independent methods. The first method utilizes a color change that occurs when p-dimethylaminocinnamaldehyde reacts with the less sterically hindered $N_1$ in the ureido portion of biotin. This reaction is very specific and only uriedo N atoms react (McCormick et al, *Analytical Biochem.*, vol. 34, pp. 226-236 (1970)). A TLC plate is dotted with 0.02 $A_{260}$ units, dried and sprayed with a 1:1 mixture of 2% sulfuric acid/ethanol and 0.2% p-dimethylaminocinnamaldehyde/ethanol and dried. A pinkish spot indicates the presence of biotin. The purified material from oligonucleotides I, II, and III (peak B) gave strong positive responses for the presence of biotin while oligonucleotide III (Peak A) gave a very weak positive response, probably due to the presence of a small amount of biotinylated material from Peak B.

Comparative Experiment IV

Oligonucleotide IV (NNNNNN, where N equals A+C+G+T) was synthesized and then biotinylated with biotinol phosphoramidite prepared as described by Alves et al (*Tetrahedron Letters*, vol. 30, pp. 3089-3092 (1989)). On purification and analysis, three peaks were found as shown by anion exchange HPLC.

All of the above-described oligonucleotides were analyzed for their binding efficiency in the second analytical method, which utilizes the very high affinity of the biotin ring for avidin. A solution of each biotinylated oligonucleotide was mixed with avidin-acrylic beads (Sigma) equilibrated with 0.02M Tris (pH 7.5)+0.2 M NaCl. The beads were allowed to settle out of solution. The percent of the oligonucleotide bound to the beads was determined by measuring the decrease in the absorbance at 260 nm of the solution above the beads when compared to the total $A_{260}$ units in the solution prior to adding the beads. The percentages of the materials bound by the beads are shown in Table I.

TABLE 1

| Oligonucleotide | % Bound |
|---|---|
| I | 89.0% |
| II | 88.1% |
| III (Peak A) | 9.5% |
| III (Peak B) | 86.5% |
| IV (Peak A) | 0 |
| IV (Peak B) | 0 |
| V (Peak C) | 37.0% |

These results indicate that biotinylation using the present reagent on a DNA synthesizer is capable of giving a DNA oligonucleotide which will withstand the conditions of ammonium hydroxide deprotection and quantitatively retain the biotin ring moiety. The binding studies indicate that biotinylation with present reagent gives a product which binds as well to avidin-acrylic beads as does an oligonucleotide biotinylated in a separate, post-synthesis reaction. Furthermore, the present reagents afford an oligonucleotide with superior binding properties in comparison to an oligonucleotide biotinylated with biotinol phosphoramidite. This latter phenomenon is probably due to the requirement for a long spacer arm to promote good binding between biotin and avidin (Hofmann et al, *Biochemistry*, vol 21, pp. 978-984 (1982)).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of the formula (I):

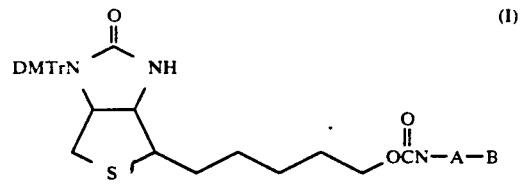

wherein A is a $-(CH_2)_mO-$ group (wherein m is an integer of 2 to 20) or a $-(C_nH_{2n}-O)_t$ group (wherein n is an integer of 2 to 6 and t is an integer of 2 to 10) and B is a group selected from the group consisting of

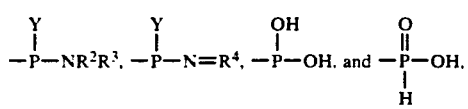

and salts thereof (wherein $R^2$ and $R^3$ are independently selected from the group consisting of $C_{3-10}$ branched alkyl groups and $C_{1-12}$ unbranched alkyl groups; $R^4$ is selected from the group consisting of $+(CRR')_r(X)_r(CCR'+_{v'}$

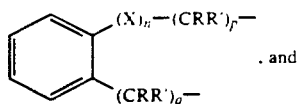
, and

(wherein R and R' are independently selected from the group consisting of H, $C_{3-10}$ branched alkyl groups, $C_{1-10}$ unbranched alkyl groups, $C_{6-10}$ aryl groups, $C_{7-12}$ alkaryl groups and $C_{7-12}$ aralkyl groups; and X is selected from the group consisting of —O—, —S—,

where R and R' are as defined above; v is an integer of 1 to 6, r is an integer of 0 to 1, p is an integer of 1 to 10, and q is an integer of 0 to 10, provided that $2v+r \leq 12$ and $2 \leq r+p+q \leq 12$; and Y is a phosphate protecting group)).

2. The compound of claim 1, wherein A is a $+CH_2-_mO+$ group and B is

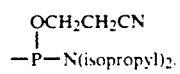

3. The compound of claim 2, wherein m is 4 to 12 and Y is —OCH₂CH₂CN.

4. The compound of claim 1 wherein A is $+CH_2+_6O-$ and B is $$-\overset{OCH_2CH_2CN}{\underset{|}{P}}-N(\text{isopropyl})_2.$$

* * * * *